United States Patent [19]
Spenlehauer et al.

[11] Patent Number: 6,120,805
[45] Date of Patent: Sep. 19, 2000

[54] MICROSPHERES, PROCESS FOR THEIR PREPARATION AND THEIR USE

[75] Inventors: Gilles Spenlehauer, Cachan; Michel Veillard, Sceaux; Thierry Verrechia, Arcueil, all of France

[73] Assignee: Rhone-Poulenc Rorer SA, Anthony Cedex, France

[21] Appl. No.: 08/455,604

[22] Filed: May 31, 1995

Related U.S. Application Data

[62] Continuation of application No. 08/122,816, Sep. 16, 1993, abandoned, which is a continuation-in-part of application No. 07/934,534, filed as application No. PCT/FR91/00274, Apr. 4, 1991, abandoned.

[30] Foreign Application Priority Data

Apr. 6, 1990 [WO] WIPO ............... PCT/FR90/04471

[51] Int. Cl.⁷ .................................................. A61K 9/16
[52] U.S. Cl. ................... 424/489; 424/499; 424/500; 424/501; 424/502; 261/4.1; 261/4.3
[58] Field of Search ..................... 424/489, 426, 424/499–502; 264/4.1, 4.3; 514/963

[56] References Cited

U.S. PATENT DOCUMENTS

| | | | |
|---|---|---|---|
| 4,330,338 | 5/1982 | Banker . | |
| 4,434,150 | 2/1984 | Azad | 424/1.1 |
| 4,818,542 | 4/1989 | De Luca et al. | 424/491 |
| 4,829,101 | 5/1989 | Kraemer | 523/201 |
| 5,069,936 | 12/1991 | Yen | 427/213.33 |
| 5,108,759 | 4/1992 | Ramey | 424/493 |
| 5,160,745 | 11/1992 | De Luca et al. | 424/499 |
| 5,302,400 | 4/1994 | Sipos | 424/494 |

FOREIGN PATENT DOCUMENTS

| | | |
|---|---|---|
| 0 134 318 | 3/1985 | European Pat. Off. . |
| 0 269 921 | 6/1988 | European Pat. Off. . |
| 0269921 | 6/1988 | European Pat. Off. . |
| 2 077 693 | 12/1981 | United Kingdom . |
| 2077693 | 12/1981 | United Kingdom . |

OTHER PUBLICATIONS

Tabata in J. of Biomedical Materials Res. 22 p. 837 (1988).

*Primary Examiner*—Gollamudi S. Kishore
*Attorney, Agent, or Firm*—Christine M. Hansen; Ross J. Oehler

[57] ABSTRACT

Biocompatible microspheres containing one or more active principals, a biodegradable and biocompatible polymer and a surface-active agent which is also biodegradable and biocompatible, contain less than 10 ppm of heavy metals. These microspheres are prepared by providing a solution of the polymer and of the active principal in a water-immiscible solvent which is more volatile than water and mixing with an aqueous solution of the surface-active agent, followed by evaporation of the solvent.

9 Claims, No Drawings

MICROSPHERES, PROCESS FOR THEIR PREPARATION AND THEIR USE

CROSS-REFERENCE TO RELATED APPLICATION

This is a continuation of application Ser. No. 8/122,816 filed on Sep. 16, 1993 now abandoned, which is a continuation-in-part application of our U.S. application Ser. No. 07/934,534 filed Oct. 6, 1992 now, abandoned, which is 371 of PCT/FR91/00274 filed Apr. 4, 1991.

FIELD OF THE INVENTION

The present invention relates to novel pharmaceutical microspheres of active principals having a particularly small diameter of the order of approximately one micron. It also relates to a process for the preparation of said microspheres and their use.

BACKGROUND OF THE INVENTION

It is particularly important in the pharmaceutical field to be able to prepare pharmaceutical preparations comprising particles having extremely small dimensions and additionally having a remarkable homogeneity of distribution. These needs are especially important for the pharmaceutical preparations intended for parenteral administration.

Certain active principals also require a coating for their administration. This leads to a double problem of obtaining pharmaceutical forms having as small a diameter as possible, the active principal being coated by a polymer and the whole necessarily being able to be administered to man or to animals. This polymer must also have properties of bio-compatibility and biodegradability.

This general problem has been known by the pharmaceutical industry for a long time. Various descriptions of microparticles have already been proposed, such as, for example, in U.S. Pat. No. 4,330,338. This patent, which does not answer the problem previously mentioned, describes a process for the preparation of polymer microspheres and their subsequent addition to pharmaceutical active principals during the preparation, for example, of tablets. According to this patent, polymer microspheres are prepared by dissolving the water-insoluble polymer in a solvent, which is more volatile than water, and this solution is then emulsified in an aqueous phase, optionally in the presence of an emulsifying agent, and the solvent is finally evaporated. The microspheres obtained have a diameter of between 0.1 to and 20 microns. They are used for coating pharmaceutical active principals. It is specified in this patent that to obtain the desired amount of coating when the polymer is insoluble in water, it is necessary to add to the emulsion an agent such as a water-soluble polymer such as, for example, methylcellulose or polyvinylpyrrolidone. These agents which favor coating are chosen from compounds which are soluble in water and acceptable for ingestion. Unfortunately, most of them are not acceptable for administration by the parenteral route. This patent never describes the coating of a pharmaceutical active principal in the form of microspheres and therefore does not resolve the problem previously mentioned.

Microspheres of active principals coated with a copolymer based on polylactic acid are also described in the EP Patent No. 269,921. These microspheres have an average diameter of between 0.1 and 10 microns. They are obtained by dissolving the polymer and the active principal to be coated in a water-immiscible solvent, followed by emulsion of the above solution in an aqueous solution containing an emulsifier and applying ultrasonic waves. The emulsifier is chosen from polyvinyl alcohol, polyvinylpyrrolidone and carboxymethylcellulose. The only emulsifier exemplified is polyvinyl alcohol. It is impossible for administration to man by the injection route to keep track of such a compound. Moreover, the use of this ultrasonification process results in an unacceptably high presence of heavy metals.

According to GB Patent No. 2,077,693, microspheres having a diameter of less than 150 $\mu$m and even of between 5 and 25 $\mu$m, which are obtained by emulsion of an organic solution of the biodegradable and biocompatible polymer and of an aqueous solution of a fatty acid salt, are also described. The fatty acid salts are not biocompatible and this patent excludes the sole presence of emulsifier, such as gelatin.

SUMMARY OF THE INVENTION

The present invention provides novel microspheres of active principal coated by a biodegradable and biocompatible polymer and by a surface-active substance which is also biodegradable and biocompatible.

The present invention further provides a process for preparing these novel microspheres comprising preparing a solution of the biodegradable and biocompatible polymer and of the active principal in a water-immiscible solvent having a volatility greater than the volatility of water and which is mixed with an aqueous solution of the surface-active agent, followed by evaporation of the water-immiscible solvent.

An injectable composition of the novel microspheres comprises about 0.05 to about 20% by weight active principal, about 0.1 to about 40% by weight polymer, about 0.2 to about 20% by weight surface-active agent and about 20 to about 99.65% by weight water.

DETAILED DESCRIPTION OF PREFERRED EMBODIMENTS

The microspheres according to the invention are made up of a base pharmaceutical active principal, of a biodegradable polymer and of a surface-active substance. Examples of pharmaceutical active principals include anti-inflammatory agents (ketoprofen, ibuprofen, salicylates), antibacterial agents (penicillins, cephalosporins, macrolides, synergistines, tetracyclines, quinolones, spiramycin), anti-cancer agents, such as taxanes, agents having an action on the heart (nitrous antianginals, antiarrhythmics, antihypertensives, beta-blockers, veinotonic agents, vasodilators),and diagnostic agents.

These microspheres are also made up of a biodegradable and biocompatible polymer, such as homopolymers of lactic acid or of glycolic acid or copolymers of said acids, polymers of polyhydroxybutyric acid, polylactones of fatty acids containing more than twelve carbon atoms (polycaprolactones, polyvalerolactones), polyorthoesters such as described by HELLER, J. Polym. Sci., 18, 619, 1980, fatty acid polyhydroxyesters having more than twelve carbon atoms (polyhydroxyvalerate), and polyanhydrides. It is presently preferred to use the copolymers of lactic acid (PLA) and of glycolic acid (GA) having a molecular weight of between 1000 and 200,000.

These microspheres are also made up of a proteinic biocompatible surface active agent, such as serum albumin, fetuin, orosomucoid, glycoproteins, immunoglobulins, gelatin, collagen, phospholipid, lipopolysaccharide or bile salts, such as sodium cholate, although other biocompatible surface-active agents may be used in accordance with the present invention.

These microspheres have a particle diameter of about 0.01 to about 10 microns and preferably about 0.05 to about 1 micron, although larger and smaller particle diameters may be used in accordance with the present invention. The active principal can equally well be situated in the center of the microsphere mixed with the biocompatible polymer or can be situated outside the center confined in the surfactant. The situation of the active principal depends greatly on its affinity for the polymer or for the surfactant.

The microspheres of the present invention are intended for pharmaceutical use. One skilled in the pharmaceutical and medical arts will appreciate that the microspheres and processes for manufacturing these microspheres should be non-toxic and pharmaceutically acceptable. Among other factors to be considered for non-toxicity and pharmaceutical acceptability is the presence of heavy metals and other metals, such as titanium, vanadium, aluminum and other metals which are pharmaceutically-unacceptable in large quantities. Preferably, the microspheres contain less than about 10 ppm of heavy metals. In addition to obviously avoiding the addition of such metals to the microspheres of the present invention, methods of processing or preparing these microparticles which introduce or increase the presence of pharmaceutically undesirable metals should be avoided.

The process for the preparation of these microspheres consists in dissolving the active principal and the polymer in an organic solvent which is immiscible with water and more volatile than water, such as, for example, halogenated solvents and dichloromethane, chloroform, toluene, aliphatic alcohols (ethanol, isopropanol), or their mixtures, although one skilled in the art will appreciate that other water-immiscible solvents which are more volatile than water may be used, depending on the solubility characteristics of the active principal and the polymer chosen.

On one side, an aqueous solution of surfactant is prepared, which is mixed at great speed with the above solution by means of a high pressure homogenizer capable of producing pressure of about $10^5$ to about $11 \times 10^5$ Pa. This technique allows the presence of heavy metals in the aqueous emulsion of microspheres to be avoided. The content of heavy metals is advantageously less than about 10 ppm.

An aqueous emulsion containing the microspheres is thus obtained which then undergoes an evaporation so as to eliminate the solvent. The microspheres obtained in aqueous solution can be used as they are or can undergo a final lyophilization step. In the last case, a lyophilization agent such as, for example, mannitol or trehalose is advantageously added.

According to a better method of carrying out the invention, a quantity of polymer which represents a concentration by weight with respect to the solvent of between 0.01 and 20% and even more preferentially of between 1 and 10% is preferably used. It is also preferred to employ at the most 25% of active principal in the mixture.

The emulsion is produced by preferably employing:
about 1 to about 50% by weight of solvent containing the polymer and the active principal,
about 98.9 to about 30% by weight of water,
about 0.1 to about 20% by weight of surface-active agent.
Even more preferentially are employed:
about 1 to about 30% by weight of solvent containing the polymer and the active principal,
about 98.9 to about 50% by weight of water,
about 0.1 to about 20% by weight of surface-active agent.
The aqueous solution obtained after evaporation of the solvent containing the microspheres is made up of:
about 0.05 to about 20% by weight of active principal,
about 0.1 to about 40% by weight of polymer,
about 0.2 to about 20% by weight of surface-active agent,
about 99.65 to about 20% by weight of water.
It is even more preferentially made up of:
about 0.05 to about 12% by weight of active principal,
about 0.1 to about 25% by weight of polymer,
about 0.1 to about 20% by weight of surface-active agent,
about 99.65 to about 57% by weight of water.
This solution can be used directly for parenteral use.

The aqueous solution obtained can also advantageously undergo a final lyophilization step after addition of approximately 10% by weight of mannitol with respect to the weight of water contained in the solution which is to undergo lyophilization.

The invention will be described in further detail by reference to the following, non-limiting examples.

EXAMPLE 1

A 1% suspension (W/W) of nanoparticles of a copolymer of D,L-lactic acid (37.5% L and 37.5% D (PLA37.5)) and glycolic acid (25% (GA25)) and of spiramycin is prepared by dissolving this polymer (0.5 g) and spiramycin (0.5 g) in dichloromethane (10 g). This solution is then dispersed in a 1% (W/W) aqueous solution of sodium cholate (50 g). A coarse emulsion is obtained. It is recycled for 3 minutes with the aid of a MICROFLUIDIX type high pressure homogenizer. The emulsion is then freed of dichloromethane with the aid of a rotary evaporator at a pressure of 50.5 cm Hg at 20° C. The pseudo-latex obtained is made up of nanoparticles of an average diameter of 60±15 nm, and contains 12.6% (W/W) of spiramycin.

EXAMPLE 2

A 7% (W/W) suspension of nanoparticles of PLA37.5 GA25 is prepared by dissolving the mixture of Example 1 (3.5 g) in dichloromethane (45 g) and following the method described in Example 1. The particles have an average diameter of 270+50 nm.

EXAMPLE 3

A 15% (W/W) suspension of nanoparticles of poly-(L)-lactic is obtained by dissolving the mixture of Example 1 (7.5 g) in dichloromethane and following the method described in Example 1.

EXAMPLE 4

A 1% (W/W) suspension of nanoparticles of polyhydroxybutyric acid and of phenoxymethylpenicillin is obtained following the method described in Example 1, replacing the sodium cholate by serum albumin, and the spiramycin by penicillin V acid (phenoxymethylpenicillin) (0.21 g). The nanoparticles contain 7.2% (W/W) of antibiotic.

EXAMPLE 5

A 1% suspension (W/W) of nanoparticles of spiramycin and of polyanhydride is obtained following the method described in Example 1, replacing the sodium cholate by a gelatin/Pluronic F68 mixture (50:50 W/W).

EXAMPLE 6

A 1% suspension (W/W) of nanoparticles of spiramycin and of PLA37.5 GA25 is obtained following the method described in Example 1, replacing the sodium cholate by purified lecithin. Observation by transmission electron microscopy reveals the presence of layers of phospholipids surrounding the polymer nanoparticles.

EXAMPLE 7

A 1% suspension (W/W) of nanoparticles of spiramycin and of poly-~caprolactone is obtained following the method described in Example 1, replacing the sodium cholate by collagen.

EXAMPLE 8

A 1% suspension (W/W) of nanoparticles of spiramycin and of PLA37.5 GA25 is obtained following the method described in Example 1, replacing the sodium cholate by fetuin.

EXAMPLE 9

A 1% suspension (W/W) of nanoparticles of spiramycin and of a copolymer of hydroxybutyric acid and valeric acid is obtained following the method described in Example 1, replacing the sodium cholate by orosomucoid.

EXAMPLE 10

A 1% suspension (W/W) of nanoparticles of spiramycin and of PLA37.5 GA25 containing cotton oil (Miglyol 812) is obtained following the method described in Example 1, adding oil (0.1 g) to the solution of polymer in the dichloromethane.

EXAMPLE 11

A 1% suspension (W/W) of nanoparticles of spiramycin and of PLA37.5 GA25 is obtained following the method described in Example 1, replacing the sodium cholate by an immunoglobulin.

EXAMPLE 12

A 1% suspension (W/W) of nanoparticles of spiramycin and of PLA37.5 GA25 is obtained following the method described in Example 1, replacing the sodium cholate by a bacterial wall lipopolysaccharide.

EXAMPLE 13

A 0.1% suspension (W/W) of nanoparticles of spiramycin and of PLA37.5 GA25 is obtained following the method described in Example 1, replacing the sodium cholate by a mixture of lecithin/ganglioside M1 (5:1, mol/mol).

EXAMPLE 14

A 0.1% suspension (W/W) of nanoparticles of spiramycin and of PLA37.5 GA25 is obtained following the method described in Example 1, replacing the sodium cholate by a high density lipoprotein.

EXAMPLE 15

A 1% suspension (W/W) of nanoparticles of spiramycin and of poly-(L)-lactic is obtained following the method of Example 1 but using a 0.05% aqueous solution of sodium cholate; the nanoparticles have an average diameter of 280+60 nm.

EXAMPLE 16

A 1% suspension (W/W) of nanoparticles of spiramycin and of poly-(D,L)-lactic is obtained following the method of Example 1 but using a 0.05% aqueous solution of serum albumin; the nanoparticles have an average diameter of 320+60 nm.

EXAMPLE 17

A 1% suspension (WbMbW) of nanoparticles of spiramycin and of poly-(D,L)-lactic is obtained following the method of Example 1 but using a 3% aqueous solution of serum albumin; the nanoparticles have an average diameter of 80±20 nm.

EXAMPLE 18 (Comparative)

In an Ultrasonics Heat System W-800 ultrasonic device, 20 ml water were introduced. Room temperature was maintained for 10 minutes while ultrasound was applied. The presence of the following were determined:

| | |
|---|---|
| Titanium | 320 μg |
| Aluminum | 22 μg |
| Vanadium | 17 μg |

EXAMPLE 19

2.375 g of a copolymer of Example 1 containing 37.5% L lactic acid, 37.5% D lactic acid and 25% glycolic acid and 0.125 g Taxotere® (docetaxel) are dissolved in 48 g dichloromethane. 2.5 g albumin are dissolved in 100 ml of a phosphate buffer at a pH of 7.4. Both solutions are mixed in a MICROFLUIDIX-type high pressure homogenizer. The emulsion is freed of dichloromethane using the same process as in Example 1. The pseudolatex is then filtered. 79 ml of filtrate is obtained with an average diameter of the particles of 159 nm. The concentration of Taxotere® in the emulsions 1.07 mg/ml and the yield of encapsulation is 86%.

After addition of 5% w/w mannitol, the emulsion is divided into 50 vials of 1 ml for lyophilization. After 5 days, the vials are solubilized with water. No particles were detected by microscope.

The present invention may be embodied in other specific forms without departing from the spirit or central attributes thereof and, accordingly, reference should be made to the appended claims, rather than to the specification, as indicating the scope of the invention.

We claim:

1. A process for preparing a composition of biocompatible microspheres, the process comprising the following steps:
    (a) preparing a first solution comprising (i) a biodegradable and biocompatible polymer, the polymer selected from the group consisting of homopolymers of lactic acid, homopolymers of glycolic acid, copolymers of lactic acid and glycolic acid, polymers of polyhydroxybutyric acid, polylactones of fatty acid containing more than twelve carbon atoms, polyorthoesters, fatty acid polyhydroxyesters having more than twelve carbon atoms, and polyanhydrides, and (ii) an active principal selected from the group consisting of anti-inflammatory agents, antibacterial agents, anticancer agents, agents having an action on the heart, and diagnostic agents, in a water-immiscible solvent, the solvent being more volatile than water;

(b) preparing a second solution in water comprising a biodegradable and biocompatible surface-active agent selected from the group consisting of serum albumin, fetuin, orosmuccoid, glycoproteins, immunoglobulins, gelatin, collagen, bile salts, phospholipid, and lipopolysaccharide;

(c) mixing the first solution with the second solution to form an aqueous emulsion by using a high pressure homogenizer capable of producing pressure of about $10^5$ to about $11 \times 10^5$ Pa; and (d) evaporating the water-immiscible solvent;

wherein the aqueous emulsion contains less than about 10 ppm of heavy metals, the microspheres have a particle diameter of between about 0.05 micron and about 1 micron, the active principal is present as about 0.05 to about 20% by weight of the composition, the biodegradable and biocompatible polymer is present as about 0.1 to about 40% by weight of the composition, the biodegradable and biocompatible surface-active agent is present as about 0.2 to about 20% by weight of the composition, and water is present as about 20 to about 99.65% by weight of the composition.

2. The microsphere produced according to the process of claim 1.

3. The composition of biocompatible microspheres produced according to the process of claim 1.

4. An injectable composition comprising the composition of claim 3.

5. The composition of claim 3, consisting essentially of (a) about 0.05 to about 12% by weight of the active principal;

(b) about 0.1 to about 25% by weight of the biodegradable and biocompatible polymer;

(c) about 0.1 to about 20% by weight of the biodegradable and biocompatible surface-active agent; and (d) about 99.65 to about 57% by weight water.

6. The composition of claim 3 comprising (a) about 0.05 to about 12% by weight of the active principal;

(b) about 0.1 to about 25% by weight of the biodegradable and biocompatible polymer;

(c) about 0.1 to about 20% by weight of the biodegradable and biocompatible surface-active agent; and (d) about 99.65 to about 57% by weight water.

7. The composition of claim 3, wherein the water-immiscible solvent is selected from the group consisting of halogenated solvents, chloroform, toluene, aliphatic alcohols and mixtures thereof.

8. The composition of claim 3, wherein the biodegradable and biocompatible polymer is a copolymer of lactic acid and glycolic acid.

9. The composition of claim 3, wherein the active principal is selected from the group consisting of taxanes, ketoprofen, ibuprofen, salicylates, penicillins, cephalosporins, macrolides, synergistines, tetracyclines, quinolones, nitrous antianginals, antiarrhythmics, antihypertensives, beta-blockers, veinotonic agents, vasodilators, and spiramycin.

* * * * *